United States Patent [19]

Downey

[11] Patent Number: 4,874,389

[45] Date of Patent: Oct. 17, 1989

[54] REPLACEMENT DISC

[76] Inventor: Ernest L. Downey, 10559 S. Ave. G., Chicago, Ill. 60617

[21] Appl. No.: 129,302

[22] Filed: Dec. 7, 1987

[51] Int. Cl.⁴ ............................................... A61F 2/44
[52] U.S. Cl. ....................................................... 623/17
[58] Field of Search ............................... 623/17, 16, 18

[56] References Cited

U.S. PATENT DOCUMENTS

| 3,593,342 | 7/1971 | Niebauer | 623/21 |
| 4,229,839 | 10/1980 | Schwemmen | 623/18 |
| 4,634,445 | 1/1987 | Helal | 623/21 |

FOREIGN PATENT DOCUMENTS

| 2263842 | 7/1974 | Fed. Rep. of Germany | 623/17 |
| 3023353 | 4/1981 | Fed. Rep. of Germany | 623/17 |
| 3535112 | 4/1987 | Fed. Rep. of Germany | 623/20 |

Primary Examiner—Richard J. Apley
Assistant Examiner—David J. Isabella
Attorney, Agent, or Firm—Frank J. Uxa, Jr.

[57] ABSTRACT

A replacement disc for use between adjacent vertebrae comprising:

a body portion having substantially opposing first and second surfaces and being adapted to fit and be held between the adjacent vertebrae; first securement means extending out from the first surface and acting to secure the replacement disc to the first adjacent vertebra; and second securement means extending out from the second surface and acting to secure the replacement disc to the second adjacent vertebra.

20 Claims, 1 Drawing Sheet

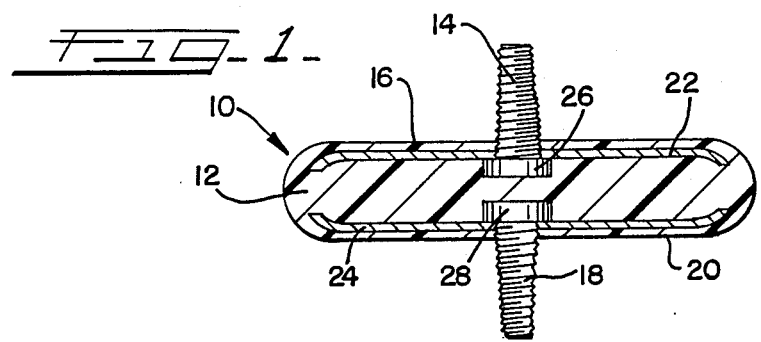
FIG-1-
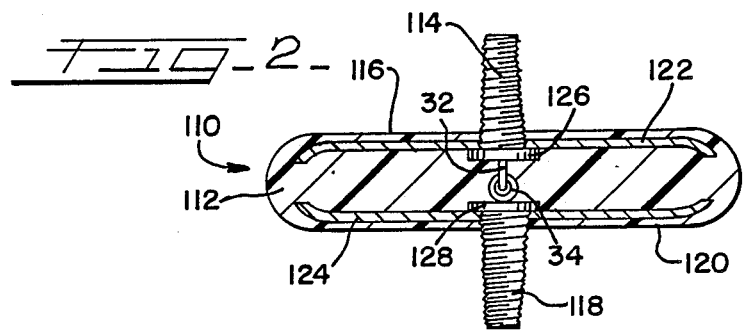
FIG-2-
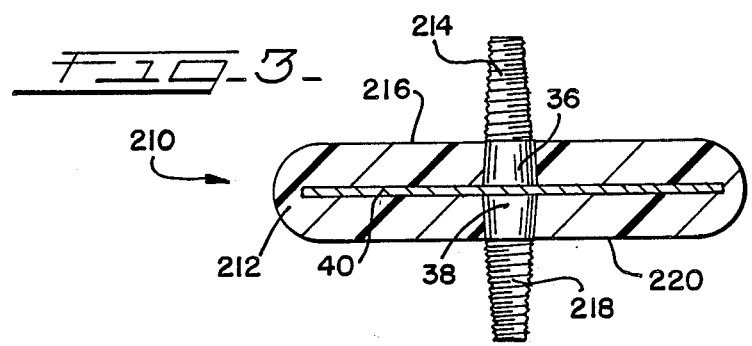
FIG-3-
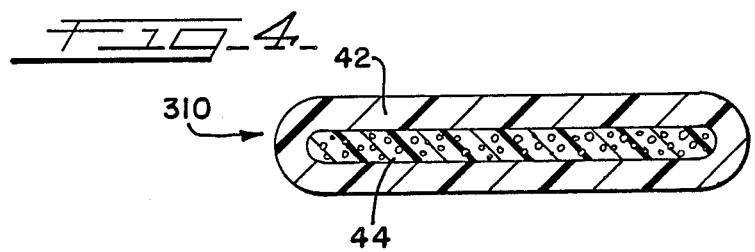
FIG-4-

REPLACEMENT DISC

The present invention relates to a replacement disc for use between two adjacent vertebrae. More particularly, this invention relates to a replacement disc which is held or secured in place between two adjacent vertebrae and acts to take the place of the natural disc material which has been removed.

One of human kind's major medical problems involves various difficulties with the back. In particular, back concerns may involve the vertebrae which are cushioned by discs which are positioned between the individual vertebrae. Because of exertion, illness, accident or abuse, one or more of these discs (or at least a portion of the disc material making up the discs) may become ruptured or is otherwise damaged and requires removal. For example, if a disc is ruptured, at least a portion of the disc material may be forced into contact with the spinal cord and/or other sensitive nerves. This contact causes excruciating pain which makes it advantageous to alleviate this condition by removing the disc material.

The ruptured disc may be surgically removed. Conventional practice has been to fuse together the vertebrae from between which the disc is removed. However, such fusing can cause a lack of flexibility in the back, especially if more than one pair of vertebrae are to be fused. It would be advantageous to provide an apparatus which can be used in place of the removed natural disc, e.g., so that fusing together of the vertebrae is not necessary.

Therefore, one object of the present invention is to provide a replacement disc for use between adjacent vertebrae. Other objects and advantages of the present invention will become apparent hereinafter.

A replacement disc for use between adjacent vertebrae to replace natural disc material, e.g., which has been removed, has been discovered. In one broad embodiment, the present replacement disc comprises an outer portion and an inner portion substantially completely surrounded by the outer portion. The inner portion is constructed of a softer, i.e., more flexible, material than the outer portion. In this embodiment, the replacement disc is sized and shaped to fit and be held between the adjacent vertebrae. Preferably, the natural tendency of the vertebrae to move toward each other, e.g., caused by the action of muscles, ligaments and the like, is sufficient to at least aid in holding the replacement disc in place between the vertebrae. In order to insure that the replacement disc is held in place, the two adjacent vertebrae may be linked together, e.g., wired and/or fused together. More preferably, the natural tendency noted above is sufficient to act as at least the primary or major means, still more preferably substantially the sole means, by which the replacement disc is held in place between the vertebrae.

Another embodiment of the present replacement disc is useful when it is desired to positively secure the replacement disc in place between the vertebrae. Broadly, this replacement disc comprises a body portion having substantially opposing first and second surfaces and being adapted to fit and be held between adjacent vertebrae; and first and second securement means. The first securement means extends out from the first surface of the body portion and acts to secure the replacement disc to one of the adjacent vertebrae. The second securement means extends out from the second surface of the body portion and acts to secure the replacement disc to the other of the adjacent vertebrae.

The present invention provides substantial advantages. For example, the present replacement discs allow injured natural disc material to be removed without necessitating vertebrae fusion. The replacement disc functions in much the same manner as does the natural disc material. Thus, the patient is relieved of the pain caused by the injured natural disc, while maintaining a substantial amount of the flexibility and freedom of action which existed prior to the natural disc becoming injured. In addition, as will be discussed in detail hereinafter, the present replacement discs can be structured to fit the particular patient involved.

In the embodiments of the present invention which include an inner portion and an outer portion, both portions are preferably made of polymeric material or materials. In any event, the material or materials of construction should be biocompatible and substantially chemically inert and insoluble in the environment in which the replacement disc is utilized. The outer portion of the replacement disc is more preferably made of silicone elastomer, in particular silastic elastomer. The inner portion is softer than the outer portion and may be made of the same or a different material as is the outer portion. For example, the inner portion may be made of a flexible (as opposed to rigid) polymeric foam or other flexible polymeric material. As used herein, the term "softer" as applied to the inner portion refers to the inner portion being more flexible or more compressible than the outer portion.

The replacement discs of the present invention which include securement means may include a body portion which has an inner portion and an outer portion, or the body portion may be substantially uniform throughout.

The material or materials of construction of the body portion should be biocompatible and substantially chemically inert and insoluble in the environment in which the replacement disc is utilized. If the body portion is substantially uniform and/or made of a single material of construction, the body portion preferably comprises silicone elastomer, in particular silastic elastomer.

The first and second securement means extend out from the first and second surfaces, respectively, of the body portion and act to secure the replacement disc to the first and second adjacent vertebrae, respectively. In one embodiment, each of the first and second securement means comprises a threaded member. In a particularly useful embodiment, the threaded member of the first securement means is threaded in the opposite direction relative to the threaded member of the second securement means. Such opposite direction threading allows the threaded members of both the first and second securement means to be threaded into both adjacent vertebrae simultaneously. This reduces the amount of manipulation required to properly set the replacement disc in place so that the body portion is fit and held between the adjacent vertebrae.

Preferably, each of the threaded members is tapered toward the end of the threaded member away from the body portion. The end of the threaded away from the body portion preferably includes a substantially flat end surface. The surface area of the end of the threaded member away from the body portion is in the range of about 30% to about 60% of the surface area of the threaded member at the surface of the body portion.

The first and second securement means preferably include a first base and a second base, respectively, each of which is located in the body portion. Such bases act to secure or anchor the securement means to the body portion. Although the first and second bases can be separate components, in one embodiment the first base and second base are parts of the same component. Such embodiment is particularly useful if it is desired to have a replacement disc of increased stiffness or reduced flexibility.

In one embodiment, the first base and the second base each extend in the body portion radially from the longitudinal axis of the first and second securement means, respectively. This radial extension feature more effectively anchors or secures the base means and securement means to the body portion.

Each of the securement means should be made of material or materials which are biocompatible and substantially inert and insoluble in the environment in which they are to be utilized. In one particularly useful embodiment, the securement means are made of metal, such as stainless steel.

The first and second securement means can be linked together, in particular by inter-engaging loop segments. Thus, for example, the bases of the first and second securement means can each terminate in a loop, which loops are linked together inside the body portion. Such inter-engaged loops provide added stability to the replacement disc and provide for increased coordination between the two adjacent vertebrae. This structure is more rigid because of the inter-engaging loop members. However, it is not as rigid as the structure in which both the first base and the second base are parts of the same component.

As can be seen from the above, the present replacement disc system can be adjusted to take into account the activity level of the medical patient in whom the disc is to be used. For example, if such patient is to, or can be expected to, engage in heavy duty activities which put substantial strain on the back or vertebrae, a system in which the first and second base means are parts of the same component or in which the first and second base means are linked together by inter-engaging loops can be used. If no heavy duty activity is anticipated, the system can be configured so that the first and second base means are entirely separated. Also, if only mild or very light activity is anticipated or if the vertebrae themselves are in such condition so that the securement means cannot be effectively utilized, a replacement disc without the securement means can be employed. Clearly the present replacement disc system can be adapted to meet a substantial variety of applications.

These and other aspects and advantages of the present invention are set forth in the following detailed description and claims particularly when considered in conjunction with the accompanying drawings in which like parts bear like reference numerals.

FIG. 1 is a side view, partially in cross section, of one embodiment of the present replacement disc.

FIG. 2 is a side view, partly in cross section, of another embodiment of the present replacement disc.

FIG. 3 is a side view, partly in cross section, of a still further embodiment of the present replacement disc.

FIG. 4 is a side view, in cross section, of yet another embodiment of the present replacement disc.

Referring now to FIG. 1, a replacement disc, shown generally at 10, includes a body 12 shaped in the form of a natural disc which is present between adjacent vertebrae, a first threaded member 14 which extends out of the first surface 16 of body 12, and a second threaded member 18 which extends out of a second surface 20 of body 12. First threaded member 14 is oppositely threaded relative to second threaded member 18.

First threaded member 14 includes a first radially extending member 22, while second threaded member 18 includes a second radially extending member 24. In addition, first threaded member 14 includes a first base element 26 while second threaded member 18 includes a second base element 28. Each of the radially extending members 22 and 24 and the base elements 26 and 28 are located within the body 12 and help to anchor or secure the threaded members 14 and 18 to the body 12. The surface area of the end of each of the threaded members 14 and 18 away from body 12 is equal to about 50% of the cross-sectional area of such members at the point where they emerge from body 12.

Body 12 is made of silastic elastomer, and all the other components noted above are made of stainless steel.

Replacement disc 10 functions as follows.

In a surgical operation, in which two adjacent vertebrae are separated, the natural disc material which is injured or otherwise requires removal is removed. One particularly useful implement for separating adjacent vertebrae is described in applicant's co-pending U.S. patent application Ser. No. 943,481, filed December 19, 1986, which is incorporated in its entirety herein by reference.

Once the natural disc material is removed, securement holes are drilled into each of the adjacent vertebrae. Such holes are shaped and sized to accommodate first threaded member 14 and second threaded member 18 respectively. After such holes have been drilled, the replacement disc is placed in the space previously occupied by the natural disc material, with the first threaded member being situated in association with one of the drilled holes and the second threaded member 18 being located in association with the second of the drilled holes. As the two vertebrae are brought back together, the body 12 is turned so as to urge each of the first threaded member 14 and second threaded member 18 into the drilled holes. After the threaded members are secured in the drilled holes, replacement disc 10 acts as the disc material between the two adjacent vertebrae.

FIG. 2 shows an alternate replacement disc 110 which includes many of the same components set forth in replacement disc 10. Except as expressly noted below, the components and functioning of alternate replacement disc 110 are substantially similar to the corresponding components and functions of replacement disc 10. For convenience, corresponding components of alternate replacement disc 110 are identified by reference numerals increased by 100 relative to the corresponding components of replacement disc 10.

Alternate replacement disc 110 includes a first loop 32 which is secured to and depends from first base element 126 and a second loop element 34 which is secured to and depends from second base element 128. First loop 32 and second loop 34 are inter-engaged or linked together. Such inter-engagement or linking together provides for increased stability in alternate replacement disc 110.

FIG. 3 shows a replacement disc 210 which includes many of the same components set forth in replacement disc 10. Except as expressly noted below, the components and functioning of replacement disc 210 are substantially similar to the corresponding components and functions of replacement disc 10. For convenience, corresponding components of alternate disc 210 are identified by reference numerals increased by 200 relative to the components of replacement disc 10.

Replacement disc 210 is structured so that the first threaded member 214 extends via a first base extension 36 into the body 212 and is joined by a second base extension 38 of second threaded member 218. A single combined radially extending member 40 is associated with both first base extension 36 and second base extension 38. Body 212 is made of silastic elastomer while the remaining components of replacement disc 210 are of stainless steel. This type of structure, which may be termed a unitary replacement disc, provides substantial rigidity to the replacement disc 210. Replacement disc 210 is of particular usefulness where a stiff arrangement between the two adjacent vertebrae is desired, for example, in situations where heavy duty activity is anticipated.

FIG. 4 shows yet another embodiment of the present replacement disc, shows generally at 310. Replacement disc 310 includes an outer portion 42 and an inner portion 44, which is completely surrounded by outer portion 42. Replacement disc 310 is shaped in the form of a natural disc which is present between adjacent vertebrae. Outer portion 38 is made of a silastic elastomer whereas inner portion 40 is made of a softer, flexible foamed polyethylene. Replacement disc 310 does not include the threaded members or associated components identified in the previous embodiments.

Replacement disc 310 is placed into the space previously occupied by the naturally occurring disc material after the adjacent vertebrae are separated. Once replacement disc 310 is so placed, the adjacent vertebrae are allowed to come together. Once the vertebrae are back in their normal position, the replacement disc 310 is held between the vertebrae by natural forces. The vertebrae can be wired or fused together to hold replacement disc 310 securely in place. Such replacement disc 310 is particularly useful where only light activity is anticipated after insertion of replacement disc 310. The other replacement discs identified above are more useful where the patient is expected to engage in heavier activity.

The components listed in each of the embodiments noted above can, for the most part, be interchanged with components in the other embodiments. For example, the embodiments shown in FIGS. 1, 2 and 3 can employ a body which includes both an outer portion and an inner portion as set forth in FIG. 4.

While this invention has been described with respect to various specific examples and embodiments it is to be understood that the invention is not limited thereto and that it can be variously practiced within the scope of the following claims.

What is claimed is:

1. A replacement disc for use between adjacent vertebrae comprising:
   a unitary body portion having substantially opposing first and second surfaces and being adapted to fit and be held between said adjacent vertebrae;
   first threaded means having a first proximal end substantially level with said first surface and a first distal end distally therefrom, said first threaded means being tapered in a direction from said first proximal end to said first distal end wherein said first distal end is about 30% to about 60% of the cross sectional area of said first proximal end; and
   second threaded means having a second proximal end substantially level with said second surface and a second distal end distally therefrom, said second threaded means being tapered in a direction from said second proximal end to said second distal end wherein said second distal end is about 30% to about 60% of the cross-sectional area of said second proximal end.

2. The replacement disc of claim 1 wherein said unitary body portion comprises a polymeric material.

3. The replacement disc of claim 1 wherein said unitary body portion comprises a silicone elastomer.

4. The replacement disc of claim 1 wherein said unitary body portion comprises a silastic elastomer.

5. The replacement disc of claim 1 wherein said first threaded means is threaded in the opposite direction relative to said second threaded means.

6. The replacement disc of claim 1 wherein said first threaded means includes a first base extending from said first proximal end, and which is located in said unitary body portion and said second threaded means includes a second base extending from said second proximal end, and which is located in said unitary body portion.

7. The replacement disc of claim 6 wherein said first base and said second base are joined together in said unitary body portion.

8. The replacement disc of claim 1 wherein said first and second threaded means each further comprise loops extending from said first and second proximal ends, respectively and which are linked together within said unitary body portion.

9. The replacement disc of claim 6 wherein said first base and said second base each extend in said unitary body portion radially from said first and second threaded means, respectively.

10. The replacement disc of claim 1 wherein each of said first and second threaded means is made of metal.

11. A replacement disc for use between adjacent vertebrae comprising:
    a unitary body portion having substantially opposing first and second surfaces and being adapted to fit and be held between said adjacent vertebrae;
    first securement means comprising a first member having a first proximal end in said unitary body portion, a first distal end extending distally from said first proximal end, and a first base located substantially entirely within said unitary body portion, secured to said first member and extending radially from said first member, said first securement means acting to secure said replacement disc to said first adjacent vertebra; and
    second securement means comprising a second member having a second proximal end in said unitary body portion, a second distal end extending distally from said second proximal end, and a second base located substantially entirely within said unitary body portion, secured to said second member and extending radially from said second member, said second securement means acting to secure said replacement disc to said second adjacent vertebra.

12. The replacement disc of claim 11 wherein said unitary body portion comprises a polymeric material.

13. The replacement disc of claim 11 wherein said unitary body portion comprises a silicone elastomer.

14. The replacement disc of claim 11 wherein said body portion comprises a silastic elastomer.

15. The replacement disc of claim 11 wherein each of said first and second members is threaded in mutually opposite directions.

16. The replacement disc of claim 11 wherein said first base and said second base are joined together in said unitary body portion.

17. A replacement disc for use between adjacent vertebrae comprising:

a unitary body portion having substantially opposing first and second surfaces and being adapted to fit and be held between said adjacent vertebrae;

first securement means comprising a first member having a first proximal end in said unitary body portion, a first distal end extending distally from said first proximal end and a first loop located in said unitary body portion, secured to said first member and extending from said first proximal end, said first securement means acting to secure said replacement disc to said first adjacent vertebra; and second securement means comprising a second member having a second proximal end in said unitary body portion, a second distal end extending distally from said second distal end and a second loop located in said unitary body portion, secured to said second member, extending from said second proximal end and linked to said first loop, said second securement means acting to secure said replacement disc to said second adjacent vertebra.

18. The replacement disc of claim 17 wherein said unitary body portion comprises a polymeric material.

19. The replacement disc of claim 17 wherein said unitary body portion comprises a silastic elastomer.

20. The replacement disc of claim 17 wherein each of said first and second members is threaded in mutually opposite directions.

* * * * *